US010750955B1

(12) United States Patent
Knickerbocker et al.

(10) Patent No.: US 10,750,955 B1
(45) Date of Patent: Aug. 25, 2020

(54) HEALTH AND FITNESS TRACKING

(71) Applicant: INTERNATIONAL BUSINESS MACHINES CORPORATION, Armonk, NY (US)

(72) Inventors: John Knickerbocker, Monroe, NY (US); Shriya Kumar, Tamil Nadu (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/299,311

(22) Filed: Mar. 12, 2019

(51) Int. Cl.
*A61B 5/0205* (2006.01)
*G16H 20/30* (2018.01)
*G16H 10/65* (2018.01)
*G16H 40/63* (2018.01)
*A61B 5/00* (2006.01)
*A61B 5/145* (2006.01)
*A61B 5/024* (2006.01)

(52) U.S. Cl.
CPC ...... *A61B 5/02055* (2013.01); *A61B 5/14532* (2013.01); *A61B 5/746* (2013.01); *A61B 5/7475* (2013.01); *G16H 10/65* (2018.01); *G16H 20/30* (2018.01); *G16H 40/63* (2018.01); *A61B 5/024* (2013.01); *A61B 2560/0247* (2013.01); *A61B 2560/0252* (2013.01)

(58) Field of Classification Search
None
See application file for complete search history.

(56) References Cited

U.S. PATENT DOCUMENTS

| 6,523,009 | B1 | 2/2003 | Wilkins |
| 8,121,855 | B2 | 2/2012 | Lorsch |
| 2010/0205005 | A1 | 8/2010 | Pritchett et al. |
| 2011/0160549 | A1* | 6/2011 | Saroka ............ A61B 5/00 600/301 |
| 2011/0301976 | A1 | 12/2011 | Davis et al. |
| 2013/0238360 | A1 | 9/2013 | Bhathal |
| 2014/0316220 | A1* | 10/2014 | Sheldon .......... A61B 5/0205 600/301 |
| 2016/0110523 | A1* | 4/2016 | Francois ......... G06Q 50/24 705/2 |

FOREIGN PATENT DOCUMENTS

WO 2014055943 4/2014

OTHER PUBLICATIONS

"SynChart—the only Personal Health Record you will ever need", Jul. 10, 2017, https://web.archive.org/web/20170710012810/https://www.synchart.com/.

* cited by examiner

*Primary Examiner* — Thomas S McCormack
(74) *Attorney, Agent, or Firm* — F. Chau & Associates, LLC

(57) ABSTRACT

A health & fitness tracking device may include a display that provides fitness information to a wearer of the health & fitness tracking device, at least one physiological sensor that obtains physiological data by monitoring at least one physiological condition of the wearer, at least one environmental sensor that obtains environmental data by monitoring at least one environmental condition, a data storage device that stores the physiological data, the environmental data, and medical history data relating to the wearer, a memory storing a computer program, and a processor that executes the computer program. The computer program may adjust a sensor configuration of the at least one physiological sensor based on the medical history data.

17 Claims, 4 Drawing Sheets

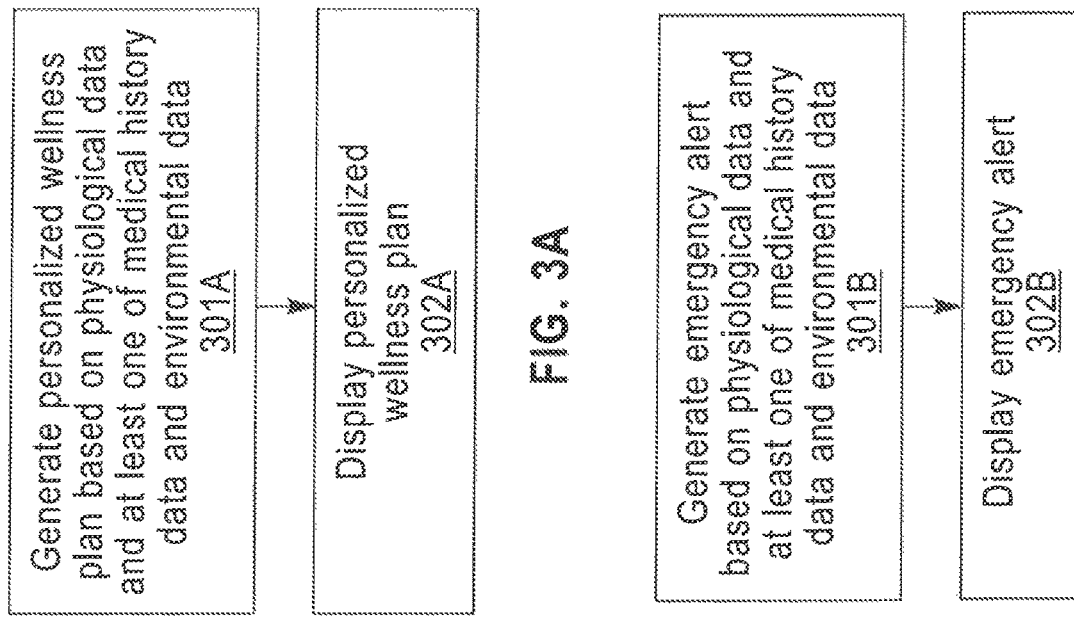
FIG. 3A
FIG. 3B
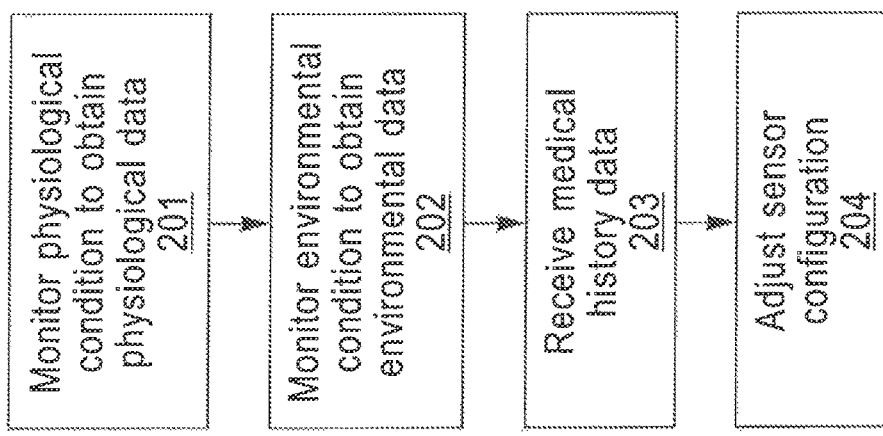
FIG. 2
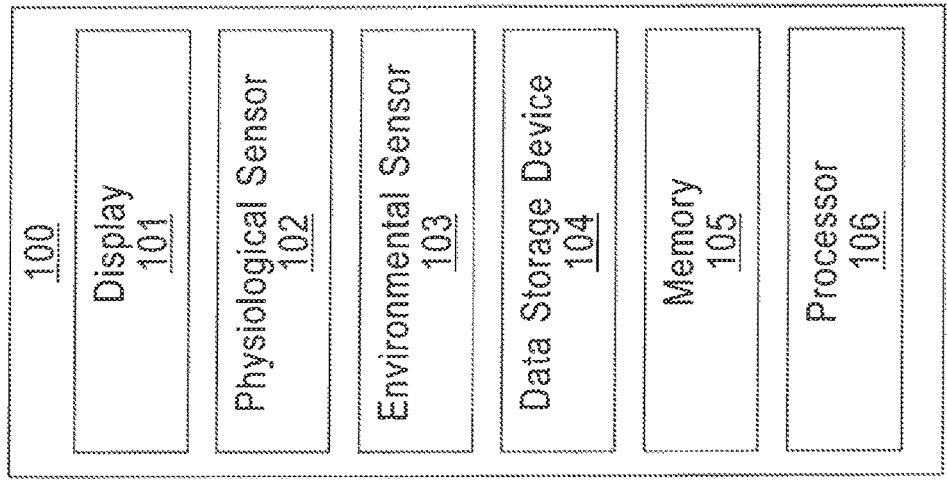
FIG. 1

HEALTH AND FITNESS TRACKING

TECHNICAL FIELD

Exemplary embodiments of the inventive concept relate to a health & fitness tracking device/diagnostic test and method of operating the health & fitness tracking device/diagnostic test.

DISCUSSION OF RELATED ART

For a given individual, medical records may originate from many different sources due to seeing different doctors or visiting different hospitals. Sometimes, records may be solely stored as hardcopy documentation. This is further complicated when taking into account the medical records of the individual's family members, which may help indicate the individual's genetic propensity for certain diseases or disorders. Additionally, this data may not be as insightful when viewed in a vacuum. Medical data of the general population or non-related individuals with similar medical characteristics may provide important reference points for comparison purposes. Moreover, other relevant medical-related data may also be stored elsewhere, e.g., DNA tests, medical test records, blood test results, death certificates, etc.

SUMMARY

According to an exemplary embodiment of the inventive concept, a health & fitness tracking device may include a display that provides health and fitness information to a user of the health & fitness tracking device, at least one physiological sensor that obtains physiological data by monitoring at least one physiological condition of the wearer, at least one environmental sensor that obtains environmental data by monitoring at least one environmental condition, a data storage device that stores the physiological data, the environmental data, and medical history data relating to the wearer, a memory storing a computer program, and a processor that executes the computer program. The computer program may adjust a sensor configuration of the at least one physiological sensor based on the medical history data.

According to an exemplary embodiment of the inventive concept, a method of operating a health & fitness tracking device may include monitoring at least one physiological condition of a wearer of the health & fitness tracking device to obtain physiological data, where the physiological data is obtained by at least one physiological sensor disposed in the health & fitness tracking device, monitoring an environmental condition to obtain environmental data, where the environmental data is obtained by at least one environmental sensor disposed in the health & fitness tracking device, receiving medical history data relating to the wearer, and adjusting a sensor configuration of the at least one physiological sensor based on the medical history data.

According to an exemplary embodiment of the inventive concept, a computer program product for operating a health & fitness tracking device may include a computer readable storage medium having program instructions embodied therewith. The program instructions may be executable by a processor to cause the processor to monitor at least one physiological condition of a wearer of the health & fitness tracking device to obtain physiological data, where the physiological data is obtained by at least one physiological sensor disposed in the health & fitness tracking device, monitor an environmental condition to obtain environmental data, where the environmental data is obtained by at least one environmental sensor disposed in the health & fitness tracking device, receive medical history data relating to the wearer, and adjust a sensor configuration of the at least one physiological sensor based on the medical history data.

BRIEF DESCRIPTION OF THE DRAWINGS

The above and other features of the inventive concept will become more apparent by describing in detail exemplary embodiments thereof, with reference to the attached drawings.

FIG. 1 is a block diagram illustrating a health & fitness tracking device according to an exemplary embodiment of the inventive concept.

FIG. 2 is a flowchart illustrating a method of operating the health & fitness tracking device of FIG. 1 according to an exemplary embodiment of the inventive concept.

FIGS. 3A and 3B are flowcharts illustrating additional operations of the method of FIG. 2 according to exemplary embodiments of the inventive concept.

DETAILED DESCRIPTION OF THE EMBODIMENTS

Figure 4:
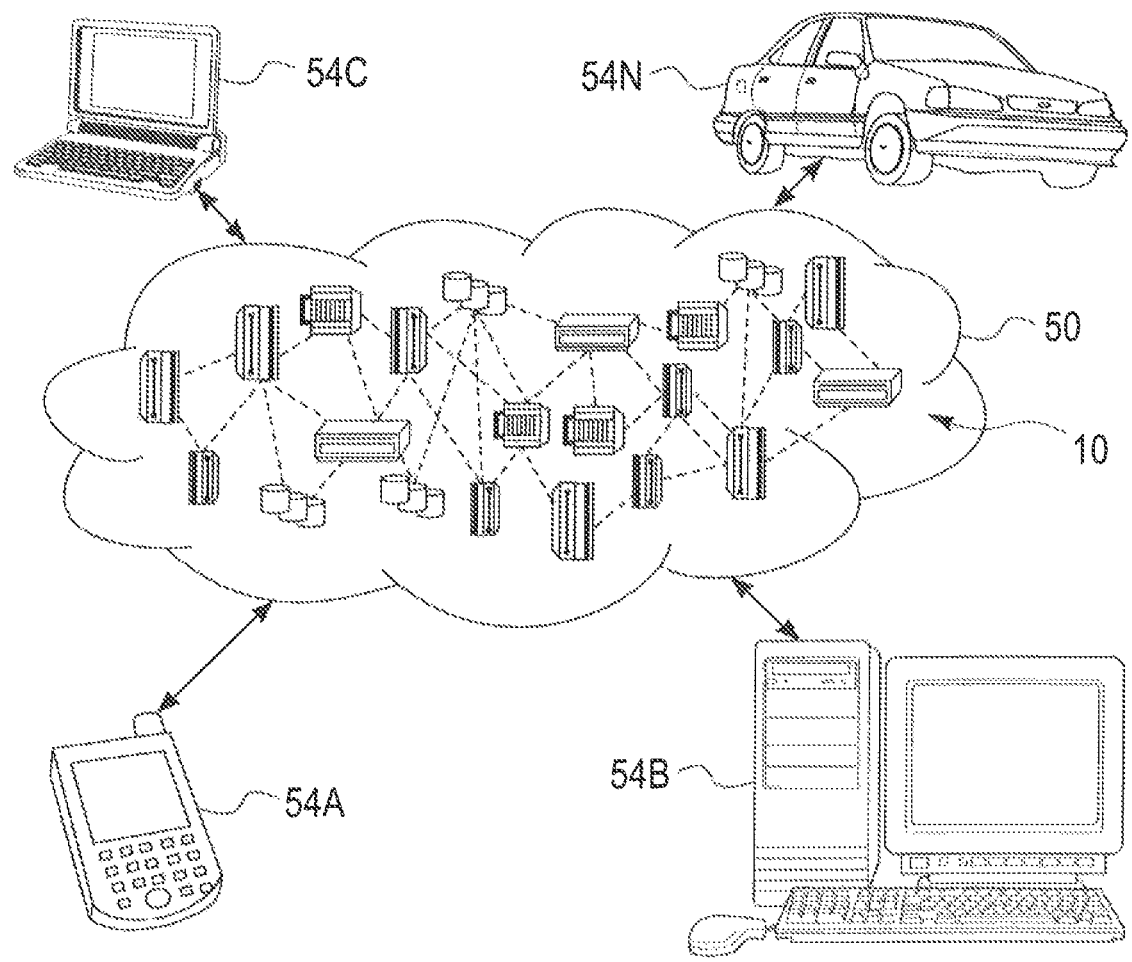
FIG. 4 depicts a cloud computing environment according to an exemplary embodiment of the inventive concept.

Consolidation of all medical-related data in an easily accessible form may provide a more complete picture for which to analyze and provide more accurate and targeted assessments, diagnoses, recommendations, suggestions, etc. to improve the health of the individual in light of the individual's current physiological condition, medical records data, trending and risk factors relative to family history (health risks such as chronic disease and/or impacts to quality of life) as well as their current environment.

Exemplary embodiments of the inventive concept relate to a health & fitness tracking device and method of operating the health & fitness tracking device. The health & fitness tracking device may have access to comprehensive medical history data of a user, and adjust a sensor configuration and/or diagnostic test & trending objectives according to the medical history data along with a current physiological/diagnostic test condition of the user and the current environment. The health & fitness tracking device may further generate a personalized wellness plan and/or an emergency alert according to the data. Accordingly, a well-rounded assessment and diagnosis of the user's health condition may be trended, predicted, and provided to the user, their family, their doctor, and/or appropriate healthcare person(s).

Exemplary embodiments of the inventive concept will be described more fully hereinafter with reference to the accompanying drawings. Like reference numerals may refer to like elements throughout the specification and drawings.

FIG. 1 is a block diagram illustrating a health & fitness tracking device according to an exemplary embodiment of the inventive concept.

Referring to FIG. 1, a health & fitness tracking device 100 may include a display 101, at least one physiological sensor 102, at least one environmental sensor 103, a data storage device 104, a memory 105, and a processor 106.

The health & fitness tracking device 100 may wearable device, e.g., a smartwatch, that may be a worn by a user. The user may be referred to as a wearer of the health & fitness tracking device 100. Alternatively, the health & fitness tracking device 100 may be a non-wearable device that performs measurements on the user and/or the environment. According to an exemplary embodiment of the inventive concept, the health & fitness tracking device 100 may be a diagnostic test system.

The display 101 may provide fitness information to the wearer of the health & fitness tracking device 100. For example, the display 101 may be a liquid crystal display (LCD), an organic light emitting display (OLED), etc.

The at least one physiological sensor 102 may obtain physiological data by monitoring at least one physiological condition and/or diagnostic test data from the wearer. According to an exemplary embodiment of the inventive concept, the at least one physiological sensor 102 may include at least one of a heart rate sensor that monitors a heart rate of the wearer, a blood glucose sensor that monitors a glucose level of the wearer, a blood diagnostic test, urine diagnostic test, a test for other body fluids, or a temperature sensor that monitors a body temperature of the wearer. However, the inventive concept is not limited thereto, and the at least one physiological sensor 102 may include other diagnostic testing bio-sensors. Additionally, the at least one physiological sensor 102 may be a noninvasive sensor. For example, the at least one physiological sensor 102 may include an optical heart-rate monitor, a galvanic skin response sensor, a thermometer, a bioimpedance sensor, an image sensor, an infrared (IR) sensor, a radar sensor, a urine diagnostic sensor/bio marker monitoring system, etc. According to an exemplary embodiment of the inventive concept, the at least one physiological sensor 102 may include two or more physiological sensors controllable by the processor 106, which will be described further below.

The at least one environmental sensor 103 may obtain environmental data by monitoring at least one environmental condition. According to an exemplary embodiment of the inventive concept, the at least one environmental sensor 103 may include at least one of an ultraviolet (UV) light sensor that monitors UV light exposure, a temperature sensor that monitors an environmental temperature, a humidity sensor that monitors a humidity level, a dust sensor that monitors a dust level, or a pollen sensor that monitors a pollen level. However, like the one or more physiological sensors 102, the inventive concept is not limited thereto, and the at least one environmental sensor 103 may include other environmental sensors.

The data storage device 104 may store the physiological data received from the at least one physiological sensor 102, the environmental data received from the at least one environmental sensor 103, and medical history data relating to the wearer, which will be described in detail below. For example, the data storage device 104 may be non-volatile memory (NVM), such as flash memory. According to an exemplary embodiment of the inventive concept, all data stored in the data storage device 104 may be encrypted.

The memory 105 may store a computer program and the processor 106 may execute the computer program. The computer program may adjust a sensor configuration of the at least one physiological sensor based on the medical history data. This will be described more fully with reference to FIGS. 2, 3A, and 3B.

According to an exemplary embodiment of the inventive concept, the health & fitness tracking device 100 may further include a wireless transceiver configured to communicate with an external device to transmit and receive data. For example, the wireless transceiver may communicate via Wi-Fi, Bluetooth, etc.

The wireless transceiver may communicate with an external computer, cloud server, etc. to access a database or repository. Communication with a cloud computing environment will be described in detail below with reference to FIGS. 4 and 5. The database may store the physiological data of the wearer, the environmental data, and the medical history data of the wearer.

According to an exemplary embodiment of the inventive concept, data stored in the database may be used by the wearer's family. For example, subsequent generations using a health & fitness tracking device like the health & fitness tracking device 100 may rely on the data for a more accurate assessment of medical risk factors. According to an exemplary embodiment of the inventive concept, a plurality of fitness tracking devices similar to the health & fitness tracking device 100 may have access to the database. As such, users may see other users' data. According to an exemplary embodiment of the inventive concept, the data in the database may be optionally anonymized for privacy reasons. Data for a plurality of users may be analyzed for statistical trends or other purposes. For example, the wearer of the health & fitness tracking device 100 may view their own health data as compared to others of the same age group, gender, etc.

According to an exemplary embodiment of the inventive concept, the database may be viewable by other individuals, e.g., doctors, nurses, medical researchers, other health professionals, etc., with appropriate authorization.

FIG. 2 is a flowchart illustrating a method of operating the health & fitness tracking device of FIG. 1 according to an exemplary embodiment of the inventive concept. FIGS. 3A and 3B are flowcharts illustrating additional operations of the method of FIG. 2 according to exemplary embodiments of the inventive concept.

Referring to FIGS. 1 and 2 together, in a method of operating the health & fitness tracking device 100, at least one physiological condition of a wearer of the health & fitness tracking device 100 may be monitored to obtain physiological data (201). The physiological data may be obtained by the at least one physiological sensor 102 disposed in the health & fitness tracking device 100, and may include heart rate, glucose level, diagnostic bio-marker test monitoring (such as urine test system or body fluid testing), or combinations thereof of the wearer, as described above. According to an exemplary embodiment of the inventive concept, the at least one physiological condition of the wearer may be monitored in real time daily, continuously, or at intervals appropriate for the wearer. For example, the monitoring may be performed at predetermined intervals, e.g., every five seconds, every hour, once a day, etc.

An environmental condition may be monitored to obtain environmental data (202). The environmental data may be obtained by the at least one environmental sensor 103 disposed in the health & fitness tracking device 100, and may include UV light exposure, environmental temperature, humidity level, etc., as described above. According to an exemplary embodiment of the inventive concept, the environmental data may be monitored in real time. However, the inventive concept is not limited thereto, and the monitoring may be performed at predetermined intervals, e.g., every five seconds, every hour, once a day, etc.

Medical history data relating to the wearer may be received (203). For example, the medical history data may include family medical history data of at least one family member of the wearer. Accordingly, the medical history data may indicate genetic risk factors faced by the wearer. As another example, the medical history data may include personal medical history data of the wearer.

The medical history data may be received from the above-described database via the wireless transceiver of the health & fitness tracking device 100. At least a portion of the medical history data may be stored locally on the health & fitness tracking device 100 (e.g., in the data storage device 104) so that the medical history data is available when the database is inaccessible.

The medical history data may originate from a variety of sources. For example, the medical history database may be manually input into a computer to be stored in the database and/or the health & fitness tracking device 100. External data such as death certificates, generational family health records, immunization records, hospital stays, genetic (DNA) data, and other medical records may be input into the database through, for example, scanning of paper/hardcopy documentation or linking with outside electronic sources (other medical databases). Accordingly, the medical history data may provide comprehensive medical information about the wearer.

For example, the medical history data may indicate whether the wearer has a history of or genetic susceptibility to diabetes, cancer, heart conditions, etc. Additionally, the medical history data may indicate whether the wearer should have additional monitoring prior to or after surgery. As such, risk factors may be identified in advance to determine which physiological conditions to monitor, which will be described further below.

In other words, an analytics process using the medical history data may determine propensities and risk factors of the wearer, along with which indicators (e.g., physiological conditions) are important to monitor for the wearer. For example, blood pressure ranges for an individual with a certain family history, body condition, and environment exposure might be different from that of the general population.

Furthermore, the analytics process may analyze and compare the medical history data with data of non-related individuals, e.g., data trends of the general population and/or people with similar medical characteristics. For example, it may be determined if the medical history data is consistent with those of similar individuals or if any of the medical history data is outside the norm. The medical history data may be updated with the comparison results. The analytics process may also continually analyze the relation between the physiological data, the environmental data, and the medical history data to continually improve the data model and provide more accurate predictions and suggestions.

According to an exemplary embodiment of the inventive concept, at least a portion of the analytics process may be performed by the health & fitness tracking device 100 itself. Additionally, an external computer may perform the analytics process and transmit results to the health & fitness tracking device 100.

According to an exemplary embodiment of the inventive concept, operations 201, 202, and 203 may be performed in any order, or at least two of operations 201, 202, and 203 may be performed substantially simultaneously.

A sensor configuration of the at least one physiological sensor 102 may be adjusted based on the medical history data (204). According to an exemplary embodiment of the inventive concept, the sensor configuration may be adjusted based on the environmental data.

As described above, the at least one physiological sensor 102 may include two or more physiological sensors, e.g., first and second physiological sensors.

As one example, in adjusting the sensor configuration, the first physiological sensor disposed in the health & fitness tracking device 100 that was previously enabled may be disabled by the computer program based on the medical history data. The second physiological sensor disposed in the health & fitness tracking device 100 that was previously disabled may be enabled by the computer program based on the medical history data.

For example, the medical history data may indicate that the wearer has a history of heart attacks but no history of diabetes. Therefore, a blood glucose sensor (e.g., the first physiological sensor) may be disabled, and a heart rate sensor and/or a blood pressure sensor (e.g., the second physiological sensor) may be enabled.

As another example, the environmental data may indicate that it is an unusually hot day. As the wearer may be at higher risk of an adverse medical condition due to the temperature, additional physiological sensors may be enabled for additional monitoring. As another example, the environmental data may indicate certain pollens, to which the wearer is allergic, are present in the air. As such, the sensor configuration may be adjusted accordingly.

In other words, the at least one physiological sensor 102 may be enabled or disabled as needed according to the medical history data and the environmental data.

According to an exemplary embodiment of the inventive concept, in adjusting the sensor configuration, a data collection frequency of the first physiological sensor may be increased based on the medical history data, and a data collection frequency of the second physiological sensor may be decreased based on the medical history data.

For example, the medical history data may indicate a history of heart attacks. Thus, data collection frequency (e.g., polling) of the heart rate sensor may be increased. On the other hand, if the medical history data indicates no history of heart attacks, the data collection frequency of the heart rate sensor may be decreased.

According to an exemplary embodiment of the inventive concept, the medical history data may include comparisons with respect to other individuals. For example, if certain data is outside the norm, the sensor configuration may be adjusted to focus on and measure related physiological attributes, e.g., the wearer has an abnormally high heart rate, abnormally low blood sugar, etc.

Referring to FIGS. 1, 2, and 3A, the method of FIG. 2 may include additional operations. A personalized wellness plan for the wearer may be generated based on the physiological data and at least one of the medical history data and the environmental data (301A).

For example, the personalized wellness plan may provide an exercise regime, nutrition recommendations, reminders to drink water, reminders to take medication, etc. The personalized wellness plan may also be synchronized with a calendar to suggest specific actions to take on particular days.

The personalized wellness plan may be output via the display 101 of the health & fitness tracking device 100 (302A). The health & fitness tracking device 100 may be configured to provide notifications (e.g., vibrations) to remind the wearer about action steps of the personalized wellness plan.

Referring to FIGS. 1, 2, and 3B, the method of FIG. 2 may include additional operations. An emergency alert for the wearer may be generated based on the physiological data and at least one of the medical history data and the environmental data (301B). For example, the physiological data may indicate a relatively high heart rate for a sustained period of time and the medical history data may indicate that the wearer has a history of heart attacks. In this case, the emergency alert may be generated.

The emergency alert may be output via the display 101 of the health & fitness tracking device 100 (302B). For example, the emergency alert may be a simple warning to the wearer to be mindful of their current condition or may provide a suggestion to see a physician as soon as possible. According to an exemplary embodiment of the inventive concept, the emergency alert may be transmitted (e.g., via the wireless transceiver described above) to a physician, a hospital, emergency services, etc. to provide assistance to the wearer.

According to an exemplary embodiment of the inventive concept, operations of FIGS. 3A and 3B may both be performed in the method of FIG. 2.

According to an exemplary embodiment of the inventive concept, the operations of FIGS. 2, 3A, and 3B may be performed by a computer. For example, in a computer program product for operating the health & fitness tracking device 100, the computer program product may include a computer readable storage medium (e.g., the storage 104 or the memory 105) having program instructions embodied therewith, and the program instructions executable by the processor 106 to cause the processor 106 to perform the above-described operations. This will be described in more detail with references to FIGS. 4-6.

Figure 5:
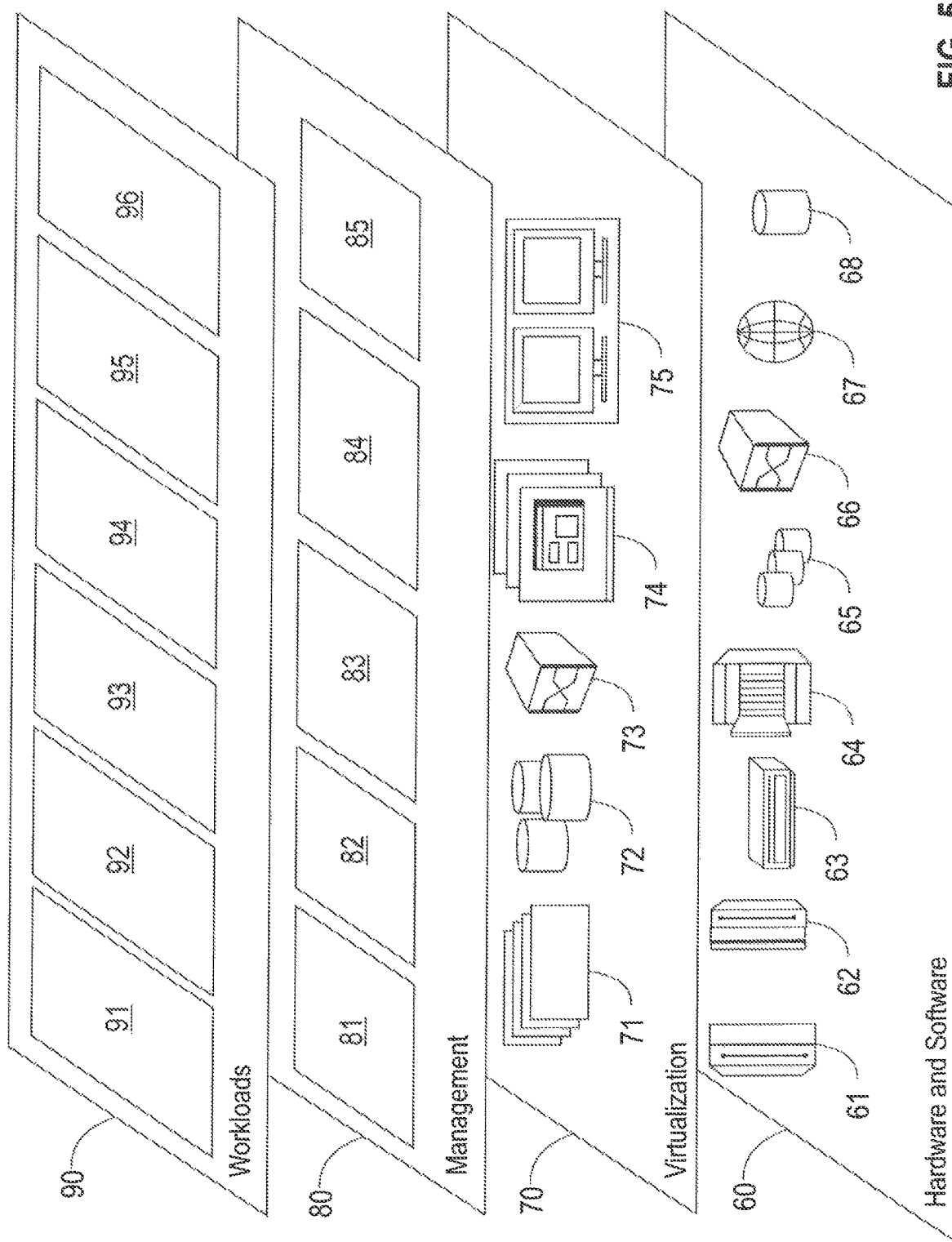
FIG. 5 depicts abstraction model layers according to an exemplary embodiment of the inventive concept.

FIG. 4 depicts a cloud computing environment according to an exemplary embodiment of the inventive concept. FIG. 5 depicts abstraction model layers according to an exemplary embodiment of the inventive concept.

It is understood in advance that although this disclosure includes a detailed description on cloud computing, implementation of the teachings recited herein are not limited to a cloud computing environment. Rather, embodiments of the inventive concept are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and a mobile desktop 96.

Figure 6:
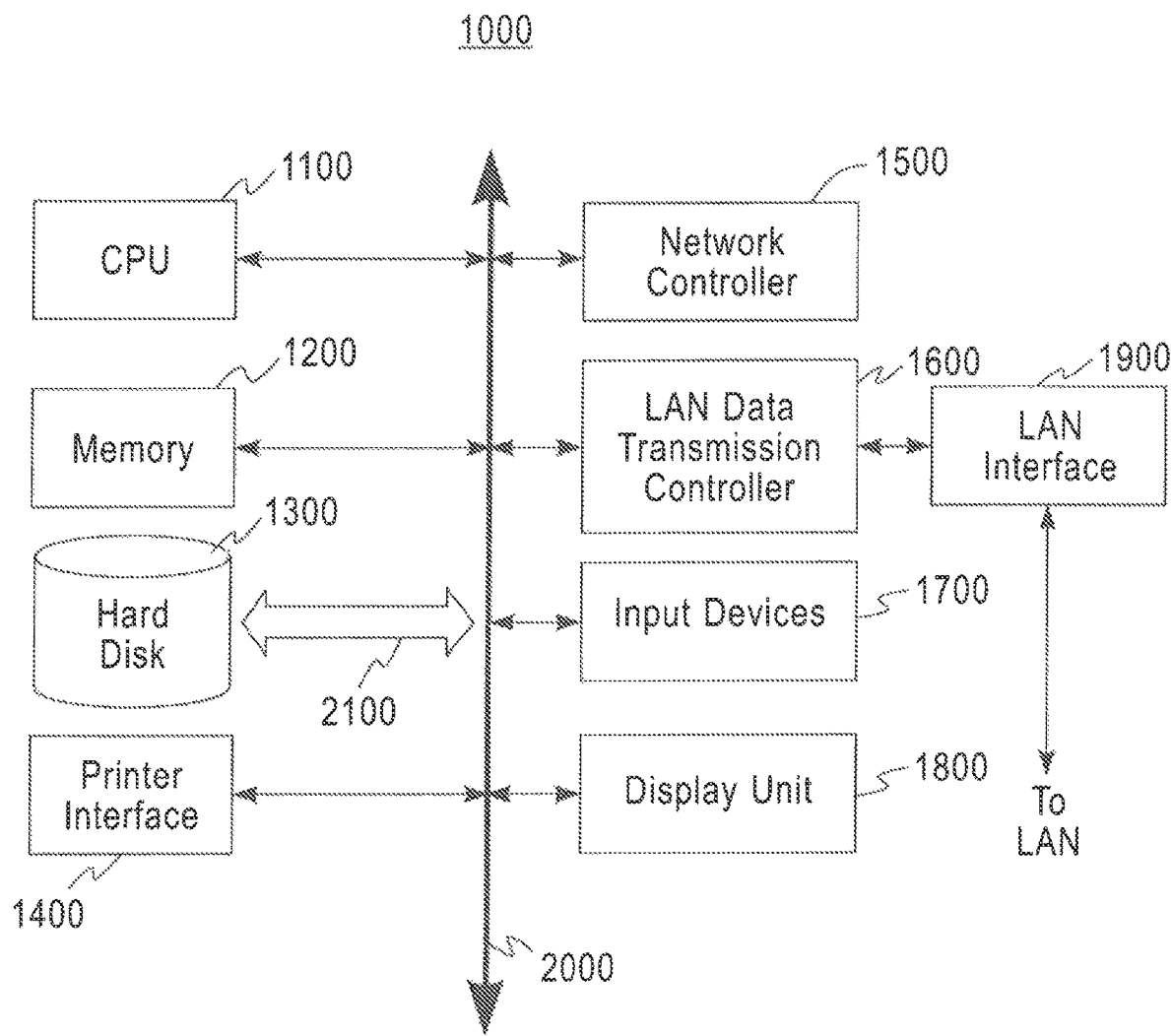
FIG. 6 illustrates an example of a computer system capable of implementing the methods according to an exemplary embodiment of the inventive concept.

FIG. 6 illustrates an example of a computer system capable of implementing the methods according to exemplary embodiments of the inventive concept. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1100, random access memory (RAM) 1200, a printer interface 1400, a network controller 1500, a local area network (LAN) data transmission controller 1600, a display unit 1800, a LAN interface 1900, an internal bus 2000, and one or more input devices 1700, for example, a keyboard, mouse etc. As shown, the system 1000 may be connected to a data storage device, for example, a hard disk, 1300 via a link 2100.

Moreover, the inventive concept may be a system, a method, and/or a computer program product at any possible technical detail level of integration. The computer program product may include a computer readable storage medium (or media) having computer readable program instructions thereon for causing a processor to carry out aspects of the inventive concept.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the inventive concept may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the inventive concept.

Aspects of the inventive concept are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the inventive concept. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

According to an exemplary embodiment of the inventive concept, with respect to the devices and methods described above with reference to FIGS. 1 to 5, they may be configured across the plurality of layers of FIG. 5 within the cloud computing environment 50 of FIG. 4. For example, the health & fitness tracking device 100 may be an additional device connected to the cloud computing environment 50. For example, the health & fitness tracking device 100 may be configured at the hardware and software layer 60. The above-described database and associated analysis processes may be configured at any of the hardware and software layer 60, the virtualization layer 70, the management layer 80, or the workloads layer 90.

According to an exemplary embodiment of the inventive concept, the health & fitness tracking device 100 may correspond to the system 1000. In this case, some elements of FIG. 6 may be excluded, e.g., the printer interface 1400, the LAN data transmission controller 1600, and the LAN interface 1900. The CPU 1100 may correspond to the processor 106, the RAM 1200 may correspond to the memory 105, the network controller 1500 may correspond to the wireless transceiver, the display unit 1800 may correspond to the display 101, and the data storage device 1300 may correspond to the data storage device 104. The input devices 1700 may correspond to the at least one physiological sensor 102 and the at least one environmental sensor 103, as well as additional buttons or a touch screen digitizer on the health & fitness tracking device 100.

As described above, according to an exemplary embodiment of inventive concept, blocks of the flowcharts illustrated in FIGS. 2, 3A, and 3B may be implemented by computer readable program instructions stored in the RAM 1200 and/or the data storage device 1300.

As described above, exemplary embodiments of the inventive concept provide a health & fitness tracking device and method of operating the health & fitness tracking device. The health & fitness tracking device may have access to comprehensive medical history data of a wearer, and adjust a sensor configuration according to the medical history data along with a current physiological condition of the wearer and a current environment. The health & fitness tracking device may further generate a personalized wellness plan and/or an emergency alert according to the data. Accordingly, a well-rounded assessment and diagnosis of the wearer's health condition may be provided. Thus, the wearer and their health care providers may take appropriate action to improve the health and wellness of the wearer.

While the inventive concept has been shown and described with reference to exemplary embodiments thereof, it will be understood by those of ordinary skill in the art that various changes in form and detail may be made therein without departing from the spirit and scope of the inventive concept as set forth by the following claims.

We claim:

1. A health & fitness tracking device, comprising:
   a display that provides health and fitness information to a wearer of the health & fitness tracking device;
   at least one physiological sensor that obtains physiological data by monitoring at least one physiological condition of the wearer;
   at least one environmental sensor that obtains environmental data by monitoring at least one environmental condition;
   a data storage device that stores the physiological data, the environmental data, and medical history data relating to the wearer;
   a memory storing a computer program; and
   a processor that executes the computer program, wherein the computer program:
   adjusts a sensor configuration of the at least one physiological sensor based on the medical history data or the environmental data;
   disables a first physiological sensor disposed in the health & fitness tracking device that was previously enabled based on the medical history data; and
   enables a second physiological sensor disposed in the health & fitness tracking device that was previously disabled based on the medical history data,
   wherein the at least one physiological sensor includes the first and second physiological sensors.

2. The health & fitness tracking device of claim 1, wherein the at least one physiological sensor comprises at least one of a heart rate sensor that monitors a heart rate of the wearer, a blood glucose sensor that monitors a glucose level of the wearer, or a temperature sensor that monitors a body temperature of the wearer.

3. The health & fitness tracking device of claim 1, wherein the at least one environmental sensor comprises at least one of an ultraviolet (UV) light sensor that monitors UV light exposure, a temperature sensor that monitors an environmental temperature, a humidity sensor that monitors a humidity level, a dust sensor that monitors a dust level, or a pollen sensor that monitors a pollen level.

4. The health & fitness tracking device of claim 1, wherein the computer program:
   increases a data collection frequency of the first physiological sensor disposed in the health & fitness tracking device based on the medical history data; and
   decreases a data collection frequency of the second physiological sensor disposed in the health & fitness tracking device based on the medical history data.

5. A method of operating a health & fitness tracking device, comprising:
   monitoring at least one physiological condition of a wearer of the health & fitness tracking device to obtain physiological data, wherein the physiological data is obtained by at least one physiological sensor disposed in the health & fitness tracking device;
   monitoring an environmental condition to obtain environmental data, wherein the environmental data is obtained by at least one environmental sensor disposed in the health & fitness tracking device;
   receiving medical history data relating to the wearer; and
   adjusting a sensor configuration of the at least one physiological sensor based on the medical history data,
   wherein adjusting the sensor configuration of the at least one physiological sensor comprises:
   disabling a first physiological sensor disposed in the health & fitness tracking device that was previously enabled based on the medical history data; and
   enabling a second physiological sensor disposed in the health & fitness tracking device that was previously disabled based on the medical history data,
   wherein the at least one physiological sensor includes the first and second physiological sensors.

6. The method of claim 5, wherein adjusting the sensor configuration of the at least one physiological sensor comprises:
   changing a data collection frequency of the at least one physiological sensor based on the medical history data.

7. The method of claim 5, further comprising:
   comparing the medical history data with medical data of people having medical characteristics similar to those of the wearer to generate a comparison result; and
   updating the medical history data based on the comparison result.

8. The method of claim 5, wherein adjusting the sensor configuration of the at least one physiological sensor comprises:
   increasing a data collection frequency of the first physiological sensor disposed in the health & fitness tracking device based on the medical history data; and
   decreasing a data collection frequency of the second physiological sensor disposed in the health & fitness tracking device based on the medical history data.

9. The method of claim 5, further comprising:
   adjusting the sensor configuration of the at least one physiological sensor based on the environmental data.

10. The method of claim 5, wherein the medical history data comprises family medical history data of at least one family member of the wearer.

11. The method of claim 5, wherein the medical history data comprises personal medical history data of the wearer.

12. The method of claim 5, further comprising:
    generating a personalized wellness plan for the wearer based on the physiological data and at least one of the medical history data and the environmental data; and
    outputting the personalized wellness plan via a display of the health & fitness tracking device.

13. The method of claim 5, further comprising:
    generating an emergency alert for the wearer based on the physiological data and at least one of the medical history data and the environmental data; and
    outputting the emergency alert via a display of the health & fitness tracking device.

14. A computer program product for operating a health & fitness tracking device, the computer program product comprising a computer readable storage medium having program instructions embodied therewith, the program instructions executable by a processor to cause the processor to:
    monitor at least one physiological condition of a wearer of the health & fitness tracking device to obtain physiological data, wherein the physiological data is obtained by at least one physiological sensor disposed in the health & fitness tracking device;
    monitor an environmental condition to obtain environmental data, wherein the environmental data is obtained by at least one environmental sensor disposed in the health & fitness tracking device;

receive medical history data relating to the wearer;
adjust a sensor configuration of the at least one physiological sensor based on the medical history data;
disable a first physiological sensor disposed in the health & fitness tracking device that was previously enabled based on the medical history data; and
enable a second physiological sensor disposed in the health & fitness tracking device that was previously disabled based on the medical history data,
wherein the at least one physiological sensor includes the first and second physiological sensors.

15. The computer program product of claim 14, wherein the program instructions executable by the processor cause the processor to:
increase a data collection frequency of the first physiological sensor disposed in the health & fitness tracking device based on the medical history data; and
decrease a data collection frequency of the second physiological sensor disposed in the health & fitness tracking device based on the medical history data.

16. The computer program product of claim 14, wherein the program instructions executable by the processor cause the processor to:
generate a personalized wellness plan for the wearer based on the physiological data and at least one of the medical history data and the environmental data; and
output the personalized wellness plan via a display of the health & fitness tracking device.

17. The computer program product of claim 14, wherein the program instructions executable by the processor cause the processor to:
generate an emergency alert for the wearer based on the physiological data and at least one of the medical history data and the environmental data; and
output the emergency alert via a display of the health & fitness tracking device.

* * * * *